United States Patent
Lee et al.

(10) Patent No.: US 11,155,875 B2
(45) Date of Patent: Oct. 26, 2021

(54) METHOD FOR DISCOVERY OF MICRORNA BIOMARKER FOR CANCER DIAGNOSIS, AND USE THEREOF

(71) Applicants: LG ELECTRONICS INC., Seoul (KR); INDUSTRY-ACADEMIC COOPERATION FOUNDATION, YONSEI UNIVERSITY, Seoul (KR)

(72) Inventors: Jaehoon Lee, Seoul (KR); Jungsu Lee, Seoul (KR); Changhee Lee, Seoul (KR); Jeeyeon Heo, Seoul (KR); Hyungseok Choi, Seoul (KR); Siyoung Song, Seoul (KR); Dawoon Jung, Seoul (KR)

(73) Assignees: LG ELECTRONICS INC., Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 470 days.

(21) Appl. No.: 15/781,958

(22) PCT Filed: Nov. 30, 2016

(86) PCT No.: PCT/KR2016/013975
§ 371 (c)(1),
(2) Date: Jun. 6, 2018

(87) PCT Pub. No.: WO2017/099414
PCT Pub. Date: Jun. 15, 2017

(65) Prior Publication Data
US 2018/0355434 A1    Dec. 13, 2018

(30) Foreign Application Priority Data

Dec. 7, 2015 (KR) .................. 10-2015-0173465
Oct. 26, 2016 (KR) .................. 10-2016-0140322

(51) Int. Cl.
*C12Q 1/6886* (2018.01)
*G16B 5/00* (2019.01)
*G16B 40/00* (2019.01)
*G16B 40/20* (2019.01)
*G16B 25/10* (2019.01)

(52) U.S. Cl.
CPC ............ *C12Q 1/6886* (2013.01); *G16B 5/00* (2019.02); *G16B 25/10* (2019.02); *G16B 40/00* (2019.02); *G16B 40/20* (2019.02); *C12Q 2600/158* (2013.01); *C12Q 2600/178* (2013.01)

(58) Field of Classification Search
CPC ........ C12Q 1/6886; G16B 5/00; G16B 25/10; G16B 40/20
USPC ......................................................... 702/19
See application file for complete search history.

(56) References Cited

U.S. PATENT DOCUMENTS

2009/0099034 A1   4/2009   Ahlquist et al.
2015/0011414 A1   1/2015   Johansen et al.

FOREIGN PATENT DOCUMENTS

WO    WO 2015/182781 A1    12/2015
WO    WO 2015/190542 A1    12/2015

OTHER PUBLICATIONS

Hübenthal et al., "Sparse Modeling Reveals miRNA Signatures for Diagnostics of Inflammatory Bowel Disease", PLOS ONE, vol. 10, No. 10, e0140155, Oct. 14, 2015, 20 pgs.
Kojima et al., "MicroRNA Markers for the Diagnosis of Pancreatic and Biliary-Tract Cancers", PLOS ONE, vol. 10, No. 2, e0118220, Feb. 23, 2015, 22 pgs.
Schrauder et al., "Circulating Micro-RNAs as Potential Blood-Based Markers for Early Stage Breast Cancer Detection," PloS One, vol. 7, No. 1, e29770, Jan. 2012 (Published Jan. 5, 2012), pp. 1-9.

*Primary Examiner* — Jerry Lin
(74) *Attorney, Agent, or Firm* — Birch, Stewart, Kolasch & Birch, LLP

(57) ABSTRACT

The present invention relates to a method for discovery of a novel miRNA biomarker for cancer diagnosis, a biomarker for diagnosis of bile duct cancer or pancreatic cancer which has been discovered through the method for discovery of a biomarker, a method for diagnosing cancer, comprising a step in which cancer is diagnosed when f(x)>0 by substitution of the expression level of the miRNA biomarker, which is detected by the method for discovery of a miRNA biomarker for cancer diagnosis, in a sample into a novel SVM classifier function, a kit for diagnosing bile duct cancer or pancreatic cancer comprising the biomarker for diagnosing bile duct cancer or pancreatic cancer, and a computing device for performing a process of diagnosing cancer when f(x)>0 as a result of a calculation by substitution of the expression level of a miRNA biomarker, which is detected by the method for discovery of a miRNA biomarker for cancer diagnosis, into the novel SVM classifier function.

3 Claims, 1 Drawing Sheet

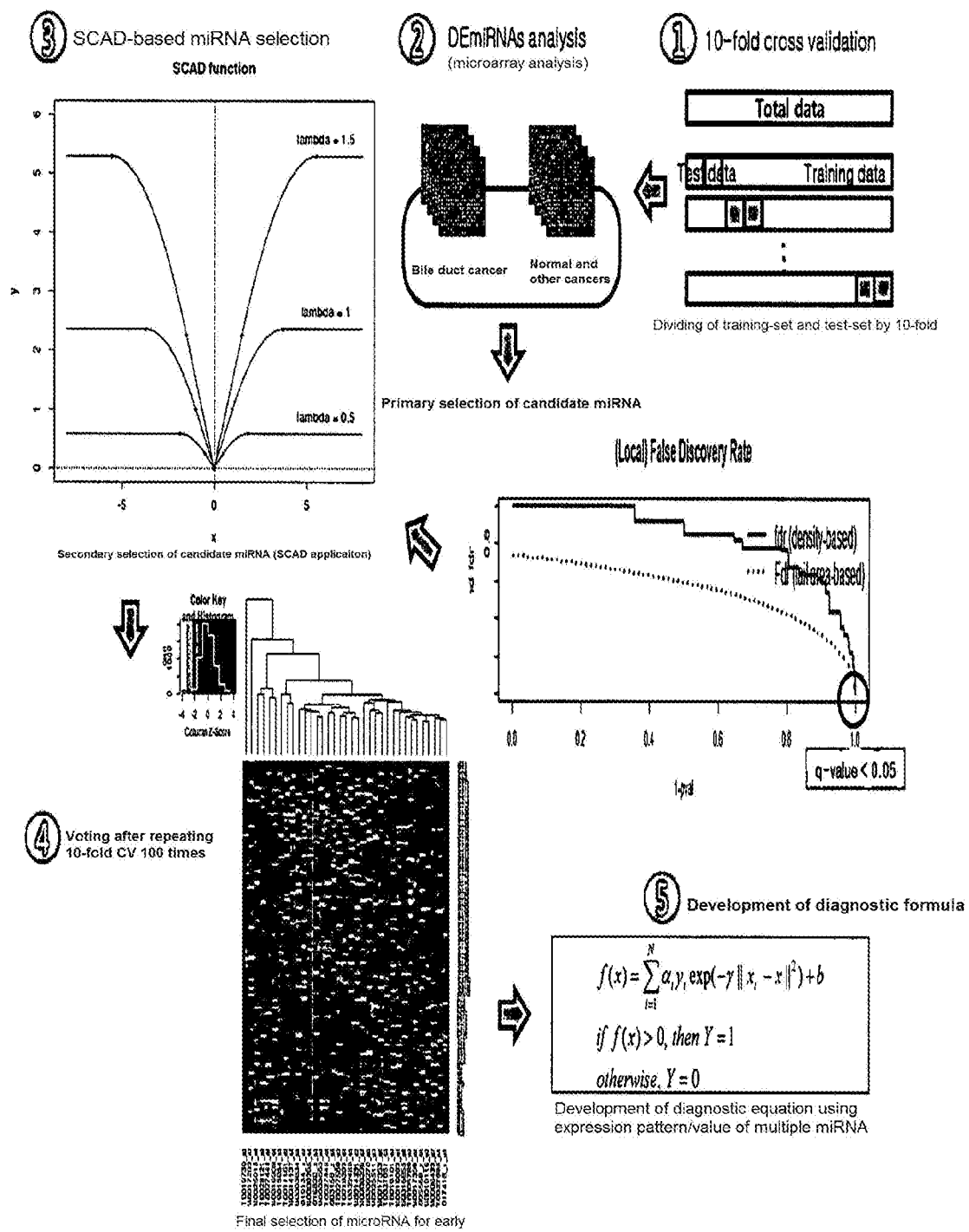

METHOD FOR DISCOVERY OF MICRORNA BIOMARKER FOR CANCER DIAGNOSIS, AND USE THEREOF

CROSS REFERENCE TO RELATED APPLICATIONS

This application is the National Phase of PCT International Application No. PCT/KR2016/013975, filed on Nov. 30, 2016, which claims priority under 35 U.S.C. 119(a) to Patent Application No. 10-2015-0173465, filed in Republic of Korea on Dec. 7, 2015 and No. 10-2016-0140322, filed in Republic of Korea on Oct. 26, 2016, all of which are hereby expressly incorporated by reference into the present application.

TECHNICAL FIELD

The present invention relates to a method for discovery of a novel miRNA biomarker for cancer diagnosis, a biomarker for diagnosis of bile duct cancer or pancreatic cancer which has been discovered through the method for discovery of a biomarker, a method for diagnosing cancer, comprising a step in which cancer is diagnosed when f(x)>0 by substitution of the expression level of the miRNA biomarker, which have been discovered by the method for discovery of a miRNA biomarker for cancer diagnosis, in a sample into a novel SVM classifier function, a kit for diagnosing bile duct cancer or pancreatic cancer comprising the biomarker for diagnosing bile duct cancer or pancreatic cancer, and a computing device for performing a process of diagnosing cancer when f(x)>0 as a result of a calculation by substitution of the expression level of a miRNA biomarker, which have been discovered by the method for discovery of a miRNA biomarker for cancer diagnosis, into the novel SVM classifier function.

BACKGROUND ART

Recently, the importance of molecular diagnostics has been gradually increased, and a clinical diagnosis of a disease (particularly, detection of an infectious pathogen, detection of mutation of a genome, detection of bicyclic cells, and identification of risk factors for a disease predisposing factor) has been explored.

In particular, through the measurement of expression of a gene in a biological sample, a nucleic acid analysis opens a new possibility which is very promising in the research and diagnosis of a disease. A nucleic acid of interest to be detected includes a genome DNA, an expressed mRNA, and other RNAs, for example, a microRNA (a miRNA).

The miRNA has emerged as an important and novel class of a regulatory RNA which deeply affects broad biological processes. These small non-coding RNA molecules may regulate the expression pattern of protein through acceleration of RNA degradation, suppression of mRNA translation, and effects on gene transcription. The miRNA plays a key role in various processes, such as development and differentiation, cell proliferation control, stress response, and metabolism. The expression of many miRNAs has been found in a modified state in numerous types of human cancers, and in some cases, a strong evidence supporting an assumption that these modifications may play a causal role in the progress of tumor has been suggested. The expression of miRNA is highly tissue-specific, and thus is also advantageous in finding the origin of a tumor tissue. Accordingly, the miRNAs may also be used as a biological marker for the purpose of research, diagnosis, and treatment.

The bile duct is a duct which delivers bile produced from the liver to the duodenum, and as branches in the liver are taken, the branches become thick while being gradually joined like gathering toward one branch, and the bile ducts on the right and left sides are mostly joined into one when the branches come out from the liver. The bile duct is divided into the intrahepatic bile duct passing through the liver and the extrahepatic bile duct escaping from the liver and leading to the duodenum. A pocket which temporarily store and concentrate bile in the extrahepatic bile duct refers to the gallbladder, and these intrahepatic and extrahepatic bile ducts and the gall collectively refer to the biliary tract.

Bile duct cancer is also called cholangiocarcinoma, which is a malignant tumor occurring in the epithelium of the bile duct, and is divided into two types of intrahepatic bile duct cancer and extrahepatic bile duct cancer according to the site of the occurrence thereof, and in general, bile duct cancer mainly indicates cancer occurring in the extrahepatic bile duct. Unless otherwise indicated in the present specification, bile duct cancer refers to both intrahepatic bile duct cancer and extrahepatic bile duct cancer.

Since bile duct cancer spreads like permeating into the surrounding tissue in many cases and does not form a clear tumor mass, it is not easy to exactly identify the mass and diagnose cancer. In general, as the image diagnosis technology develops, bile duct cancer has been diagnosed by using a technology such as abdominal ultrasonography, computed tomography (CT), magnetic resonance imaging (MRI), percutaneous transhepactic cholangiogram (PTC), percutaneous transhepatic biliary drainage (PTBD), endoscopic retrograde cholangiopancreatography (ERCP), or angiography.

The pancreas is present in the posterior of the stomach and in the middle of the body, and the strength thereof is as long as 20 cm. The pancreas is surrounded by organs such as the stomach, the duodenum, the small intestine, the large intestine, the liver, the gall, and the spleen. The total length thereof is about 15 to 20 cam, the weight thereof is approximately 100 g, and the pancreas is classified into the head, the body, and the tail. The pancreas has an exocrine function of secreting digestive enzymes which degrade carbohydrate, fat, and protein in the ingested food, and an endocrine function of secreting hormones such as insulin and glucagon, which regulate the blood sugar.

Pancreatic cancer is a lump consisting of cancer cells generated in the pancreas. The pancreatic cancer is classified into various types, and pancreatic ductal adenocarcinoma occurring in the pancreatic cells occupies 90% of the cancer, so that pancreatic cancer generally refers to pancreatic ductal adenocarcinoma. In addition, there are cystadenocarcinoma, endocrinoma, and the like.

Since pancreatic cancer does not have any specific initial symptom, it is difficult to early find pancreatic cancer. The appetite drops, body weight loss, and the like occur, but these symptoms are not characteristic of pancreatic cancer, and thus, may sufficiently occur even in other diseases.

Further, since the pancreas has a thickness as thin as 2 cm, is surrounded by only thin films, and is closely adhered to the superior mesenteric artery which supplies oxygen to the small intestine, the hepatic portal vein which conveys nutrients absorbed from the gut to the liver, and the like, the infiltration of cancer easily occurs. In addition, pancreatic cancer has a characteristic in that even in the nerve fascicle in the posterior of the pancreas and the lymph gland, the metastasis thereof occurs at the early stage. In particular, the pancreatic cancer cells have a fast growth speed. When a disease develops, the patient lives only for 4 months to 8 months in most cases, and the prognosis is not good and even though the symptoms get better due to the success in operation, the chance of survival for 5 years or more is as low as approximately 17 to 24%.

Pancreatic cancer is diagnosed through ultrasonography, computed tomography (CT), magnetic resonance imaging (MRI), endoscopic retrograde cholangiopancreatography (ERCP), endoscopic ultrasonography (EUS) and/or proton emission tomography (PET). However, since these image diagnostic technologies are highly costly in diagnosis, complicated, and practically useless for early diagnosis, there is a need for a means which is simple and economically feasible in terms of costs and can be early diagnosed.

Thus, there is an urgent need for development of a biomarker, particularly, for bile duct cancer and pancreatic cancer, which has high sensitivity and specificity, and thus can reliably diagnose cancer and can be utilized in an actual diagnosis, and a precise diagnosing method using the same.

DISCLOSURE OF THE INVENTION

Therefore, an object of the present invention is to provide a method for discovery of a miRNA biomarker for cancer diagnosis, the method including: (i) screening differential expression miRNAs in a sample by using a microarray analysis; (ii) rescreening the detected differential expression miRNAs by applying an SCAD penalty function; and (iii) selecting one or more of the rescreened differential expression miRNAs as a biomarker by being compared with a sensitivity and specificity calculation result of a cancer prediction model.

Another object of the present invention is to provide a biomarker for diagnosis of bile duct cancer or pancreatic cancer which has been discovered through the method for discovery of a miRNA biomarker for cancer diagnosis.

Still another object of the present invention is to provide a method for diagnosing cancer, the method including: a step in which cancer is diagnosed when f(x)>0 by substitution of the expression level of a miRNA biomarker, which has been discovered through the method for discovery of a miRNA biomarker for cancer diagnosis, in a sample into a novel SVM classifier function.

Yet another object of the present invention is to provide a kit for diagnosing bile duct cancer or pancreatic cancer, the kit including the biomarker for diagnosing bile duct cancer or pancreatic cancer.

Still yet another object of the present invention is to provide a computing device including: a storing part for storing data; and a control part for calculation, in which the control part performs a process of diagnosing cancer when f(x)>0 as a result of a calculation by substitution of the expression level of a miRNA biomarker, which has been discovered through the method for discovery of a miRNA biomarker for cancer diagnosis, into a novel SVM classifier function.

To achieve these and other advantages and in accordance with the purpose of the present invention, as embodied and broadly described herein, there is provided a method for discovery of a miRNA biomarker for cancer diagnosis according to an Example of the present invention includes: (i) screening differential expression miRNAs in a sample by using a microarray analysis; (ii) rescreening the screened differential expression miRNAs by applying an SCAD penalty function; and (iii) selecting one or more of the rescreened differential expression miRNAs as a biomarker based on a sensitivity and specificity calculation result of a cancer prediction model.

In the method for discovery of a miRNA biomarker for cancer diagnosis, the sample may be a peripheral blood sample.

One or more steps in Steps (i) to (iii) may be performed by a 10-fold cross validation one or more times.

Step (i) may consist of screening a miRNA in which a q-value determined through a multiple test adjustment is less than 0.05.

The biomarker for diagnosing bile duct cancer according to another Example of the present invention is:

(i) one or more selected from the group consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p; or (ii) one or more selected from the group consisting of miRNA hsa-miR-7107-5p, hsa-miR-4270, hsa-miR-1268a, hsa-miR-3162-3p, and hsa-miR-6729-5p; or (iii) a combination of (i) and (ii), which have been discovered through the method for discovery of a miRNA biomarker for cancer diagnosis.

The biomarker for diagnosing pancreatic cancer according to another Example of the present invention is:

(i) one or more selected from the group consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p; or (ii) one or more selected from the group consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p; or (iii) a combination of (i) and (ii), which have been discovered through the method for discovery of a miRNA biomarker for cancer diagnosis.

The method for cancer discovery according to still another Example of the present invention includes: a step in which cancer is diagnosed when f(x)>0 with cancer by substitution of the expression level of a miRNA biomarker, which has been discovered through the method for discovery of a miRNA biomarker for cancer diagnosis, in a sample into a novel SVM classifier function.

$$f(x) = \sum_{i=1}^{n} \alpha_i y_i \exp(-\gamma \|x_i - x\|^2) + b$$

(in the equation, $y_i$ means a y value of an i-th support vector, $x_i$ means an x value of the i-th support vector, $\alpha_i$ means a weight of the i-th support vector, N means the number of support vectors, γ is a shape parameter of a radial basis function kernel, b is an intercept of a decision function, and x means a miRNA expression level vector of a patient to be diagnosed.)

In the method for diagnosing cancer, the sample may be a peripheral blood sample.

The diagnosis method may be performed by substitution of the expression level of each miRNA biomarker in the peripheral blood sample into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p, and a subject to be diagnosed may be bile duct cancer.

The diagnosis method may be performed by substitution of the expression level of each miRNA biomarker in a peripheral blood sample into an SVM classifier function for a biomarker set consisting of miRNA hsa-miR-7107-5p, hsa-miR-4270, hsa-miR-1268a, hsa-miR-3162-3p, and hsa-miR-6729-5p, and a subject to be diagnosed may be bile duct cancer.

The diagnosis method may be performed by substitution of the expression level of each miRNA biomarker in a peripheral blood sample into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, hsa-miR-888-3p, hsa-miR-7107-5p, hsa-miR-4270, hsa-miR-1268a, hsa-miR-3162-3p, and hsa-miR-6729-5p, and a subject to be diagnosed may be bile duct cancer.

The diagnosis method may be performed by substitution of the expression level of each miRNA biomarker in a peripheral blood sample into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p, and a subject to be diagnosed may be pancreatic cancer.

The diagnosis method may be performed by substitution of the expression level of each miRNA biomarker in a peripheral blood sample into an SVM classifier function for a biomarker set consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

The diagnosis method may be performed by substitution of the expression level of each miRNA biomarker in a peripheral blood sample into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, hsa-miR-425-3p, hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

The kit for diagnosing bile duct cancer according to yet another Example of the present invention includes a biomarker which is:

(i) one or more selected from the group consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p; or (ii) one or more selected from the group consisting of miRNA hsa-miR-7107-5p, hsa-miR-4270, hsa-miR-1268a, hsa-miR-3162-3p, and hsa-miR-6729-5p; or (iii) a combination of (i) and (ii), which have been discovered through the method for discovery of a miRNA biomarker for cancer diagnosis.

The kit for diagnosing pancreatic cancer according to yet another Example of the present invention includes a biomarker which is:

(i) one or more selected from the group consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p; or (ii) one or more selected from the group consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p; or (iii) a combination of (i) and (ii), which have been discovered through the method for discovery of a miRNA biomarker for cancer diagnosis.

A computing device according to still yet another Example of the present invention includes: a storing part for storing data; and a control part for calculation, in which the control part performs a process of diagnosing cancer when $f(x)>0$ as a result of a calculation by substitution of the expression level of a miRNA biomarker, which has been discovered through the method for discovery of a miRNA biomarker for cancer diagnosis, into the following SVM classifier function.

$$f(x) = \sum_{i=1}^{n} \alpha_i y_i \exp(-\gamma \|x_i - x\|^2) + b$$

(in the equation, $y_i$ means a y value of an i-th support vector, $x_i$ means an x value of the i-th support vector, $\alpha_i$ means a weight of the i-th support vector, N means the number of support vectors, $\gamma$ is a shape parameter of a radial basis function kernel, b is an intercept of a decision function, and x means a miRNA expression level vector of a patient to be diagnosed.)

The control part may calculate an expression level of each miRNA biomarker in a peripheral blood sample by substitution of the expression level into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p, and a subject to be diagnosed may be bile duct cancer.

The control part may calculate an expression level of each miRNA biomarker in a peripheral blood sample by substitution of the expression level into an SVM classifier function for a biomarker set consisting of miRNA hsa-miR-7107-5p, hsa-miR-4270, hsa-miR-1268a, hsa-miR-3162-3p, and hsa-miR-6729-5p, and a subject to be diagnosed may be bile duct cancer.

The control part may calculate an expression level of each miRNA biomarker in a peripheral blood sample by substitution of the expression level into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, hsa-miR-888-3p, hsa-miR-7107-5p, hsa-miR-4270, hsa-miR-1268a, hsa-miR-3162-3p, and hsa-miR-6729-5p, and a subject to be diagnosed may be bile duct cancer.

The control part may calculate an expression level of each miRNA biomarker in a peripheral blood sample by substitution of the expression level into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p, and a subject to be diagnosed may be pancreatic cancer.

The control part may calculate an expression level of each miRNA biomarker in a peripheral blood sample by substitution of the expression level into an SVM classifier function for a biomarker set consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

The control part may calculate an expression level of each miRNA biomarker in a peripheral blood sample by substitution of the expression level into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, hsa-miR-425-3p, hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

Hereinafter, the present invention will be described in more detail.

In an exemplary embodiment, the present invention provides a method for discovery of a miRNA biomarker for cancer diagnosis, the method including: (i) screening differential expression miRNAs in a sample by using a microarray analysis; (ii) rescreening the screened differential expression miRNAs by applying an SCAD penalty function; and (iii) selecting one or more of the rescreened differential expression miRNAs as a biomarker based on a sensitivity and specificity calculation result of a cancer prediction model.

The method for discovery of a biomarker for cancer diagnosis according to the present invention first begins from a step of screening miRNAs by detecting miRNAs differentially expressed from cancer patients, that is, expressed differently from the normal; in other words, expressed extremely high or extremely low as compared to a normal expression level.

The term "differential expression" refers to a qualitative or quantitative difference in gene expression pattern according to the time and/or according to the cell between cell and tissue and in cell and tissue. That is, the gene differentially expressed may be, for example, a gene in which the expression is qualitatively modified by including activation or non-activation in a normal tissue vs. a disease tissue. The gene can compare two or more states because the expression can be turned on or turned off in a specific state as compared to other states. The gene qualitatively regulated may exhibit an expression pattern capable of being detected by a standard technology in a certain state or cell type. Some genes may be expressed only in one state or one cell type, and may be expressed in neither one state nor one cell type. Otherwise, the difference in expression may be quantitative, for example, in that the expression level is adjusted such that the expression is upregulated, and thus the amount of transcript is increased or the expression is downregulated, and thus the amount of transcript is decreased. Accordingly, the differential expression may include, for example, both quantitative and qualitative differences in temporary or cellular expression pattern in a normal cell and a disease cell, or a cell experiencing a different disease phenomenon or disease step. Further, the differential expression from the viewpoint of methodology thereof may be analyzed by a comparison of expression between two or more genes or gene products thereof; or a comparison of expression rate between two or more genes or gene products thereof; or even a comparison of products differently treated from different and the same genes between a normal individual and an individual suffering from a disease; or a comparison of products differently treated from the different and the same gene in various steps of the same disease.

The expression profile used in the present invention may refer to a genome expression profile, for example, an expression profile of a miRNA. The profile may be produced by any convenient means which measures the level of a nucleic acid sequence, such as a quantitative hybridization, a quantitative PCR and an ELISA for quantification, of as a miRNA, a labeled miRNA, an amplified miRNA, an ncRNA, and the like, and a differential gene expression between two samples may be analyzed by using the means. The sample is taken by any convenient method publicly known in the art. An expression profile may be based on the measurement of the level of nucleic acid, or may also be based on a score which is obtained by combining these measured values.

The present invention is a method, which basically uses a miRNA as an expression profile and discovers a biomarker through an analysis according to the expression level thereof. Since a miRNA related to a specific disease (for example, cancer) is present, and the miRNA generally serves to suppress the expression of a gene, the present invention is based on a negative (−) relationship in which the expression level of the miRNA is inversely proportional to the expression level of a specific gene which is related to the expression level of the miRNA. Further, since some miRNAs serve to increase the expression of a gene, the present invention is based on a positive (+) relationship in which the expression level of the miRNA in this case is proportional to the expression level of a specific gene which is related to the expression level of the miRNA.

The method for discovery of a biomarker by the miRNA according to the present invention is first subjected to a step of matching the expression levels of the miRNA of humans including a normal person and a number of patients with cancer (may be a specific cancer). Here, the miRNA may be a miRNA of the entire human, and may also be a miRNA pool that is suspected to be related to a target disease among them. A miRNA which is not practically related to the target disease may also be included in these miRNAs. Therefore, among these miRNAs, there is a need for a procedure of screening a miRNA as a biomarker capable of being suitably used for a disease analysis or evaluation. For this purpose, the screening is related to the target disease, and can be selected by comparison using a publicly-known miRNA, which is already known. The screening may be complemented through a correlation analysis of a miRNA known to a person of ordinary skill in the art with the expression of a gene.

In the method for discovery of a biomarker according to the present invention, the screening may include a screening which performs a t-test comparing an average of the expression levels of a miRNA of a normal group with an average of the expression levels of a miRNA of a specific cancer group.

The method is a method for statistically significantly finding out the differential expression miRNA and uses a linear model which is one of the high-level statistical methods, which may consider various factors. The method may be again divided into a data normalization step and a statistical analysis step. The data normalization step is a step of integrating and correcting microarray data for the miRNAs of humans obtained from a normal person group and a patient group. For the data normalization, a robust multichip average (RMA) algorithm may be used. The statistical analysis step is a step of screening a miRNA in which there is a statistically significant difference in expression level between the two groups (that is, the normal person group and the patient group) by using a linear model as the normalized data.

In conclusion, when a t-test (significance level 0.05) is performed on the expression levels of the miRNAs of the patient group and the normal person group, it can be seen that there is a significant difference between the patient group and the normal person group when a specific miRNA comes within a significance level range, and the miRNA may be an effective candidate for a biomarker. In comparison with this, the miRNA in which the significance level exceeds a standard range cannot be an effective biomarker.

As a result of the aforementioned t-test, a p-value comes for each miRNA. However, since the test is an effort of the statistical analysis and there are a large number of miRNAs to be an analysis target, the p-value needs to be corrected through a multiple test adjustment.

When a number of statistical tests are performed, for example, in comparison of signals between the two groups under a number of data characteristics, a possibility that a wrong positive result may be obtained is gradually increased by a random difference between the groups which may reach a level which is considered to be statistically significant as another method. In order to limit the false discovery rate, the statistical significance is limited only to data characteristics reaching a p-value (a value by t-tests on both sides) in which the difference is less than a critical value, and the critical value depends on the number of tests performed and the distribution of p-values obtained from these tests.

Even though a test result comes out with a 5% significance level with respect to whether there is a statistically significant difference between the two groups, it cannot be concluded that when the test group becomes three or more, the test groups are significant equally to the case the test group becomes two within a 5% significance level. For a result that there are N groups and Group 1 is significantly different from the other groups N−1 within p<0.05, the number of cases which may be a test which is determine as a false among the N−1 tests in total is (N−1)*0.05, and the test may be a test which is determined as a false as much as the number. Accordingly, in the case of a multiple test, the test needs to be performed by a more rigorous standard without finishing the analysis with a p-value of 0.05, and this is called as a post hoc. In the post hoc, various methods have been suggested (Bonferroni's, Duncan's, and the like), but in the present invention, a false discovery rate (FDR) which is not extremely preservative may be used.

In conclusion, the q-value may be thought as a p-value in consideration of a false discovery (false positive, Type I error) at the time of performing a multiple test. Unlike a general statistics which tests one or two hypotheses, when a large amount of a microarray and the like are simultaneously tested as in the present invention, an absolutely large number of errors are committed when a wrong decision is made in spite of a type I error as low as 0.05, so that even 0.05 or 0.01, which is a p-value frequently used, becomes extremely large, and accordingly, the value needs to be corrected, and a value obtained by correcting the p-value suitably for these situations may be defined as a q-value.

In the method for discovery of a biomarker of the present invention, a statistically significant probability in screening a target miRNA may be set as a q-value of 0.05 or less, which is a p-value corrected by using the FDR, and the smaller the value is, the more significant the value becomes as a miRNA which is expressed differently from a normal value. Accordingly, Step (i) may consist of screening a miRNA in which a q-value determined through a multiple test adjustment is less than 0.05. Preferably, Step (i) may consist of screening a miRNA in which a q-value determined through a multiple test adjustment is less than 0.05.

In a specific exemplary embodiment, Step (i) may be performed by a 10-fold cross validation (CV) one or more times. When a test is conducted by using the same data after constructing a model without dividing a training test and a test data, a model becomes excessively suitable, so that the reliability of the result may deteriorate. In order to prevent this, data are equally divided into 10, and then 9/10 is randomly designated as training data, 1/10 is randomly designated as test data, and the data which are repeated 10 times are designated as a 10-fold cross validation, and in order to enhance the reliability of screening of the miRNA screened in Step (i) of the method for delivery of a biomarker according to the present invention, an analysis result may be derived from each training set by applying the 10-fold cross validation. In this case, a more reliable result value may be obtained by performing the 10-fold cross validation one or more times, for example, 10 times, for examples, 100 times.

As described above, Step (i) may be completed by screening a miRNA in which a q-value (for each training data) is less than 0.05, preferably, less than 0.01.

In the method for discovery of a biomarker of the present invention, the miRNAs primarily screened may be seen as miRNAs selected in consideration of each individual significance of the miRNA, and Step (ii) may be seen as a step of rescreening a more significant miRNA as a diagnostic biomarker in simultaneous consideration of a number of miRNAs by a smoothly clipped absolute deviation (SCAD) penalty function.

When big data or high-dimensional data are dealt with, the algorithm performance may be more stably and easily interpreted by only reducing the high dimension into the low dimension and a number of variables into a small number. There may be various variable selection methods for this purpose, but it is a penalty method that has been highlighted with the development of the computer calculation ability. In the present invention, the miRNA may be rescreened by using an SCAD penalty method having statistically good properties. For example, when total 100 variables such as x1, x2, x3, . . . x100 are assumed to affect a y value, if data are analyzed by using the SCAD method in the case where x values which more affect the y value among these values are desired to be selected, variables which greatly affect the y value among the 100 variables may be selected, and when the variables are used, the variable which has the highest influence may be easily selected in the case where various variables are simultaneously present. That is, when the SCAD penalty function is applied to the miRNA primarily screened in Step (i), more significant miRNAs may be secondarily rescreened as a biomarker which diagnoses the corresponding cancer (Step (ii)).

Next, in Step (iii), one or more among the differential expression miRNA candidates rescreened by being subjected to Step (ii) are selected as a final biomarker based on the result of calculating the sensitivity and specificity of a cancer prediction model.

The term "sensitivity" may refer to a statistical measurement value for how well correctly a binary classification test identifies the situation, for example, how frequently correctly cancer is classified into a more correct type between the two possible types. The sensitivity for A classification is measured based on certain absolute criteria and is a ratio of a case which is decided to belong to "A" classification by the test to the cases belonging to "A" classification.

The term "specificity" may refer to a statistical measurement value for how well correctly a binary classification test identifies the situation, for example, how frequently correctly cancer is classified into a more correct type between the two possible types. The specificity for A classification is measured based on certain absolute criteria and is a ratio of a case which is decided to belong to "being not A" classification by the test to the cases belonging to "being not A" classification.

Step (iii), which is a step of selecting a final miRNA biomarker, may consist of an order which is the highest in prediction performance by calculating each sensitivity and specificity for candidate miRNA upper rankers screened up to Step (ii).

For example, in the case of bile duct cancer, a possibility that a patient with bile duct cancer is predicted as a patient with bile duct cancer may refer to sensitivity, and a possibility that a normal person is predicted as normal may refer to specificity, and it is possible to select a final miRNA biomarker for bile duct cancer in the order (close to an area of 1 under a curve of the ROC curve for the sensitivity and specificity) which is the best in prediction performance thereof by calculating the sensitivity and specificity for bile duct cancer among the miRNA biomarker candidates secondarily screened.

Likewise, as in Step (i), in a specific exemplary embodiment, Step (ii) or Step (iii) may be also performed by a 10-fold cross validation (CV) one or more times, and, for example, a more reliable result value may be obtained by performing the 10-fold cross validation 10 times, for example, 100 times. For example, k candidates, which are the best in prediction performance, may be selected as a final miRNA biomarker by repeating the 10-fold cross validation 100 times, selecting a candidate miRNA for each training data, ranking the candidate miRNAs in order of frequency, and then calculating each of sensitivity and specificity of a cancer prediction model using the upper k candidates.

In another exemplary embodiment, the present invention provides a biomarker for diagnosing bile duct cancer. In the present invention, a biomarker for diagnosing bile duct cancer was discovered by the method for discovery of a biomarker of the present invention, and these are:

(i) one or more selected from the group consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p; or (ii) one or more selected from the group consisting of miRNA hsa-miR-7107-5p, hsa-miR-4270, hsa-miR-1268a, hsa-miR-3162-3p, and hsa-miR-6729-5p; or (iii) a combination of (i) and (ii). The sequence information on these is shown in the following Table 1 and Table 2.

TABLE 1

| No | miRNA ID | miRNA Accession Number | Sequence |
|---|---|---|---|
| 1 | hsa-miR-26b-5p | MIMAT0000083 | UUCAAGUAAUUCAGGAUAGGU |
| 2 | hsa-miR-214-5p | MIMAT0004564 | UGCCUGUCUACACUUGCUGUGC |
| 3 | hsa-miR-191-3p | MIMAT0001618 | GCUGCGCUUGGAUUUCGUCCCC |
| 4 | hsa-miR-127-5p | MIMAT0004604 | CUGAAGCUCAGAGGGCUCUGAU |
| 5 | hsa-miR-128-2-5p | MIMAT0031095 | GGGGGCCGAUACACUGUACGAGA |
| 6 | hsa-miR-580-5p | MIMAT0026617 | UAAUGAUUCAUCAGACUCAGAU |
| 7 | hsa-miR-593-5p | MIMAT0003261 | AGGCACCAGCCAGGCAUUGCUCAGC |
| 8 | hsa-miR-653-3p | MIMAT0026625 | UUCACUGGAGUUUGUUUCAAUA |
| 9 | hsa-miR-1224-3p | MIMAT0005459 | CCCCACCUCCUCUCUCCUCAG |
| 10 | hsa-miR-208b-5p | MIMAT0026722 | AAGCUUUUUGCUCGAAUUAUGU |
| 11 | hsa-miR-1229-5p | MIMAT0022942 | GUGGGUAGGGUUUGGGGGAGAGCG |
| 12 | hsa-miR-548g-3p | MIMAT0005912 | AAAACUGUAAUUACUUUUGUAC |
| 13 | hsa-miR-513c-5p | MIMAT0005789 | UUCUCAAGGAGGUGUCGUUUAU |
| 14 | hsa-miR-1825 | MIMAT0006765 | UCCAGUGCCCUCCUCUCC |
| 15 | hsa-miR-3126-5p | MIMAT0014989 | UGAGGGACAGAUGCCAGAAGCA |
| 16 | hsa-miR-3649 | MIMAT0018069 | AGGGACCUGAGUGUCUAAG |
| 17 | hsa-miR-3677-3p | MIMAT0018101 | CUCGUGGGCUCUGGCCACGGCC |
| 18 | hsa-miR-499b-5p | MIMAT0019897 | ACAGACUUGCUGUGAUGUUCA |
| 19 | hsa-miR-4770 | MIMAT0019924 | UGAGAUGACACUGUAGCU |
| 20 | hsa-miR-4784 | MIMAT0019948 | UGAGGAGAUGCUGGGACUGA |
| 21 | hsa-miR-5687 | MIMAT0022478 | UUAGAACGUUUUAGGGUCAAAU |
| 22 | hsa-miR-5697 | MIMAT0022490 | UCAAGUAGUUUCAUGAUAAAGG |
| 23 | hsa-miR-6511a-3p | MIMAT0025479 | CCUCACCAUCCCUUCUGCCUGC |
| 24 | hsa-miR-6740-3p | MIMA10027382 | UGUCUUCUCUCCUCCCAAACAG |
| 25 | hsa-miR-6773-5p | MIMAT0027446 | UUGGGCCCAGGAGUAAACAGGAU |
| 26 | hsa-miR-6795-3p | MIMAT0027491 | ACCCCUCGUUUCUUCCCCCAG |
| 27 | hsa-miR-6814-3p | MIMAT0027529 | ACUCGCAUCCUUCCCUUGGCAG |
| 28 | hsa-miR-6843-3p | MIMAT0027588 | AUGGUCUCCUGUUCUCUGCAG |
| 29 | hsa-miR-6884-3p | MIMAT0027669 | CCCAUCACCUUUCCGUCUCCCCU |
| 30 | hsa-miR-6889-3p | MIMAT0027679 | UCUGUGCCCCUACUUCCCAG |
| 31 | hsa-miR-6892-5p | MIMAT0027684 | GUAAGGGACCGGAGAGUAGGA |
| 32 | hsa-miR-7158-5p | MIMAT0028226 | GGCUCAAUCUCUGGUCCUGCAGCC |
| 33 | hsa-miR-208a-3p | MIMAT0000241 | AUAAGACGAGCAAAAAGCUUGU |
| 34 | hsa-miR-888-3p | MIMAT0004917 | GACUGACACCUCUUUGGGUGAA |

TABLE 2

| No | miRNA ID | miRNA Accession Number | Sequence |
|---|---|---|---|
| 1 | hsa-miR-7107-5p | MIMAT0028111 | UCGGCCUGGGGAGGAGAAGGG |
| 2 | hsa-miR-4270 | MIMAT0016900 | UCAGGGAGUCAGGGGAGGGC |
| 3 | hsa-miR-1268a | MIMAT0005922 | CGGGCGUGGUGGUGGGGG |
| 4 | hsa-miR-3162-3p | MIMAT0019213 | UCCCUACCCCUCCACUCCCCA |
| 5 | hsa-miR-6729-5p | MIMAT0027359 | UGGGCGAGGGCGGCUGAGCGGC |

In addition, in another exemplary embodiment, the present invention provides a biomarker for diagnosing pancreatic cancer. In the present invention, a biomarker for diagnosing pancreatic cancer was discovered by the method for discovery of a biomarker of the present invention, and these are:

(i) one or more selected from the group consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p; or (ii) one or more selected from the group consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p; or (iii) a combination of (i) and (ii). The sequence information on these is shown in the following Table 3 and Table 4.

TABLE 3

| No | miRNA ID | miRNA Accession Number | Sequence |
|---|---|---|---|
| 1 | hsa-miR-378b | MIMAT0014999 | ACUGGACUUGGAGGCAGAA |
| 2 | hsa-miR-27b-3p | MIMAT0000419 | UUCACAGUGGCUAAGUUCUGC |
| 3 | hsa-miR-191-3p | MIMAT0001618 | GCUGCGCUUGGAUUUCGUCCCC |
| 4 | hsa-miR-5583-5p | MIMAT0022281 | AAACUAAUAUACCCAUAUUCUG |
| 5 | hsa-miR-3145-5p | MIMAT0019205 | AACUCCAAACACUCAAAACUCA |
| 6 | hsa-miR-513a-5p | MIMAT0002877 | UUCACAGGGAGGUGUCAU |
| 7 | hsa-miR-877-5p | MIMAT0004949 | GUAGAGGAGAUGGCGCAGGG |
| 8 | hsa-miR-2053 | MIMAT0009978 | GUGUUAAUUAAACCUCUAUUUAC |
| 9 | hsa-miR-3183 | MIMAT0015063 | GCCUCUCUCGGAGUCGCUCGGA |
| 10 | hsa-miR-490-5p | MIMAT0004764 | CCAUGGAUCUCCAGGUGGGU |
| 11 | hsa-miR-4310 | MIMAT0016862 | GCAGCAUUCAUGUCCC |
| 12 | hsa-miR-642b-3p | MIMAT0018444 | AGACACAUUUGGAGAGGGACCC |
| 13 | hsa-miR-1269b | MIMAT0019059 | CUGGACUGAGCCAUGCUACUGG |
| 14 | hsa-miR-5571-5p | MIMAT0022257 | CAAUUCUCAAAGGAGCCUCCC |
| 15 | hsa-miR-933 | MIMAT0004976 | UGUGCGCAGGGAGACCUCUCCC |
| 16 | hsa-miR-5692a | MIMAT0022484 | CAAAUAAUACCACAGUGGGUGU |
| 17 | hsa-miR-6069 | MIMAT0023694 | GGGCUAGGGCCUGCUGCCCCC |
| 18 | hsa-miR-548ay-5p | MIMAT0025452 | AAAAGUAAUUGUGGUUUUUGC |
| 19 | hsa-miR-6763-5p | MIMAT0027426 | CUGGGGAGUGGCUGGGGAG |
| 20 | hsa-miR-6854-3p | MIMAT0027609 | UGCGUUUCUCCUCUUGAGCAG |
| 21 | hsa-miR-6854-5p | MIMAT0027608 | AAGCUCAGGUUUGAGAACUGCUGA |

TABLE 3-continued

| No | miRNA ID | miRNA Accession Number | Sequence |
|---|---|---|---|
| 22 | hsa-miR-7154-5p | MIMAT0028218 | UUCAUGAACUGGGUCUAGCUUGG |
| 23 | hsa-miR-425-3p | MIMAT0001343 | AUCGGGAAUGUCGUGUCCGCCC |

TABLE 4

| No | miRNA ID | miRNA Accession Number | Sequence |
|---|---|---|---|
| 1 | hsa-miR-1228-3p | MIMAT0005583 | UCACACCUGCCUCGCCCCCC |
| 2 | hsa-miR-1469 | MIMAT0007347 | CUCGGCGCGGGGCGCGGGCUCC |
| 3 | hsa-miR-4530 | MIMAT0019069 | CCCAGCAGGACGGGAGCG |
| 4 | hsa-miR-4532 | MIMAT0019071 | CCCCGGGGAGCCCGGCG |
| 5 | hsa-miR-4721 | MIMAT0019835 | UGAGGGCUCCAGGUGACGGUGG |
| 6 | hsa-miR-4741 | MIMAT0019835 | UGAGGGCUCCAGGUGACGGUGG |
| 7 | hsa-miR-486-5p | MIMAT0002177 | UCCUGUACUGAGCUGCCCCGAG |
| 8 | hsa-miR-5100 | MIMAT0022259 | UUCAGAUCCCAGCGGUGCCUCU |
| 9 | hsa-miR-5787 | MIMAT0023252 | GGGCUGGGGCGCGGGGAGGU |
| 10 | hsa-miR-6087 | MIMAT0023712 | UGAGGCGGGGGGGCGAGC |
| 11 | hsa-miR-642a-3p | MIMAT0020924 | AGACACAUUUGGAGAGGGAACC |
| 12 | hsa-miR-642b-3p | MIMAT0018444 | AGACACAUUUGGAGAGGGACCC |
| 13 | hsa-miR-6800-5p | MIMAT0027500 | GUAGGUGACAGUCAGGGGCGG |
| 14 | hsa-miR-6803-5p | MIMAT0027500 | GUAGGUGACAGUCAGGGGCGG |
| 15 | hsa-miR-7704 | MIMAT0030019 | CGGGGUCGGCGGCGACGUG |
| 16 | hsa-miR-6808-5p | MIMAT0027516 | CAGGCAGGGAGGUGGGACCAUG |

The term "biological sample" used in the present invention refers to a sample of a biological tissue or a biological fluid, which includes nucleic acids. These samples are not limited thereto, but a tissue or a fluid, which is separated from a subject, is included. A tissue section such as a biopsy or autopsy sample, an FFPE sample, and a frozen section, blood, plasma, serum, sputum, feces, tears, mucus, hair, and skin taken for the histological purpose may also be included in the biological sample. A primary and/or transformed cell culture and explant derived from an animal or patient tissue may also be included in the biological sample. The biological sample may also be a cell content of blood, blood fraction, urine, exudate, abdominal dropsy, saliva, cerebrospinal fluid, cervical secretion, vaginal secretion, gastrointestinal secretion, bronchial secretion, sputum, cell lines, tissue samples, and fine needle aspiration (FNA), or secretion from the breast. The biological sample may be supplied by cutting out a cellular sample from an animal, but a cell isolated in advance (for example, a cell separated by the third person, at another time point, and/or for another purpose) can be used, or a tissue recorded in a document, such as a tissue having a treatment or result history, can also be used.

The tissue sample is a tissue obtained from a tissue biopsy using methods publicly known to those of ordinary skill in the related medical arts, and examples of a method of obtaining a sample by a biopsy include a gross apportioning of a mass by the unaided eye, microdissection, microdissection based on laser, or other cell separation methods publicly known in the art.

In a specific exemplary embodiment, the sample in the method of discovery of a miRNA biomarker for cancer diagnosis may be a peripheral blood sample, and the peripheral blood sample is commonly considered as a sample capable of being taken by a non-invasive method, and thus has an advantage in that the method may be more friendly to the human body while escaping from a tissue collection method which is inefficient and accompanies pains.

In still another exemplary embodiment, the present invention provides a method for diagnosing cancer, the method including: a step in which cancer is diagnosed when f(x)>0 by substitution of the expression level of a miRNA biomarker, which has been discovered through the method for discovery of a miRNA biomarker for cancer diagnosis, in a sample into the following SVM classifier function.

$$f(x) = \sum_{i=1}^{n} \alpha_i y_i \exp(-\gamma \|x_i - x\|^2) + b$$

(in the equation, $y_i$ means a y value of an i-th support vector, $x_i$ means an x value of the i-th support vector, $\alpha_i$ means a weight of the i-th support vector, N means the number of support vectors, γ is a shape parameter of a radial basis function kernel, b is an intercept of a decision function, and x means a miRNA expression level vector of a patient to be diagnosed.)

Specifically, $y_i$ means a y value of an i-th support vector, that is, whether there is a disease, and the cancer is 1, and the normal is −1.

$x_i$ means an x value of the i-th support vector, that is, an expression level vector of a miRNA biomarker, and the vector has elements as many as the number of miRNA biomarkers.

$\alpha_i$ means a weight of the i-th support vector. The larger the value is, the higher the weight contributing to the SVM sorter the i-th support vector becomes.

N means the number of support vectors.

γ means a shape parameter of a radial basis function (RBF) kernel. The value is obtained by a separate 10-fold cross validation. The higher the value is, the more pointed shape the hyperplane exhibits. The RBF kernel is a non-linear kernel most generally used in the SVM.

b means an intercept of a decision function.

x means a miRNA expression level vector of a patient to be diagnosed, and the vector has elements as many as the number of miRNA biomarkers.

In the present invention, the SVM classifier function was developed as a diagnostic formula capable of early diagnosing cancer. The SVM diagnosis model consists of SVM support vector $x_i$ (i=1, N) values, a classified value $y_i$ corresponding to each support vector, and parameters $\alpha_i$ (i=1, . . . , N), N, γ, b, and x.

The SVM classifier function f(x) developed in the present invention is a function capable of exhibiting whether a subject patient comes down with a specific cancer according to the relationship between the SVM support vector and the miRNA biomarker for the specific cancer discovered by the above-described method for discovery of a biomarker of the present invention. When each expression level of a biomarker miRNA for a specific cancer extracted from a patient in need of diagnosis for the specific cancer is defined as $x=(x1, x2, \ldots xN)^T$, it is possible to predict that by substitution of the value into the function, an f(x) larger than 0 is the specific cancer and an f(x) smaller than 0 is normal.

In a specific exemplary embodiment, the diagnosis method may be performed by a biomarker set (total 34 ea.) for bile duct cancer, which consists of hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p. It is possible to predict that by substitution of the expression level of each miRNA biomarker in a peripheral blood sample into an SVM classifier function, when f(x)>0 by substitution of x1, x2, . . . , x34, which is each expression level of 34 miRNAs into the function, the case is bile duct cancer (Y=1), and the case where f(x) is not >0 is normal (Y=0).

In a specific exemplary embodiment, the diagnosis method may be performed on a biomarker set (total 5 ea.) for bile duct cancer, which consists of miRNA hsa-miR-7107-5p, hsa-miR-4270, hsa-miR-1268a, hsa-miR-3162-3p, and hsa-miR-6729-5p. It is possible to predict that by substitution of the expression level of each miRNA biomarker in a peripheral blood sample into an SVM classifier function, when f(x)>0 by substitution of x1, x2, . . . , x5, which is each expression level of 5 miRNAs into the function, the case is bile duct cancer (Y=1), and the case where f(x) is not >0 is normal (Y=0).

In a specific exemplary embodiment, the diagnosis method may be performed by a biomarker set (total 39 ea) for bile duct cancer, which consists of hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, hsa-miR-888-3p, hsa-miR-7107-5p, hsa-miR-4270, hsa-miR-1268a, hsa-miR-3162-3p, and hsa-miR-6729-5p. It is possible to predict that by substitution of the expression level of each miRNA biomarker in a peripheral blood sample into an SVM classifier function, when f(x)>0 by substitution of x1, x2, . . . , x39, which is each expression level of 39 miRNAs into the function, the case is bile duct cancer (Y=1), and the case where f(x) is not >0 is normal (Y=0).

In a specific exemplary embodiment, the diagnosis method may be performed on an a biomarker set (total 23 ea) for pancreatic cancer, which consists of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p. It is possible to predict that by substitution of the expression level of each miRNA biomarker in a peripheral blood sample into an SVM classifier function, when f(x)>0 by substitution of x1, x2, . . . , x23, which is each expression level of 23 miRNAs into the function, the case is pancreatic cancer (Y=1), and the case where f(x) is not >0 is normal (Y=0).

In a specific exemplary embodiment, the diagnosis method may be performed on a biomarker set (total 16 ea) for pancreatic cancer, which consists of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p. It is possible to predict that by substitution of the expression level of each miRNA biomarker in a peripheral blood sample into an SVM classifier function, when f(x)>0 by substitution of x1, x2, . . . , x16, which is each expression level of 16 miRNAs into the function, the case is pancreatic cancer (Y=1), and the case where f(x) is not >0 is normal (Y=0).

In a specific exemplary embodiment, the diagnosis method may be performed on a biomarker set (total 39 ea) for pancreatic cancer, consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, hsa-miR-425-3p, hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p. It is possible to predict that by substitution of the expression level of each miRNA biomarker in a peripheral blood sample into an SVM classifier function, when f(x)>0 by substitution of x1, x2, . . . , x39, which is each expression level of 39 miRNAs into the function, the case is bile duct cancer (Y=1), and the case where f(x) is not >0 is normal (Y=0).

In a specific exemplary embodiment, the sample in the method for diagnosing cancer may be a peripheral blood sample likewise as in the method for discovery of a biomarker of the present invention. Since an advantage in the case where a peripheral blood sample capable of being taken by a non-invasive method is used has been described in detail, the advantage will be omitted.

In another exemplary embodiment, the present invention provides a kit for diagnosing bile duct cancer. The kit includes one or more biomarkers selected from the group consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p, which have been discovered through the method for discovery of a miRNA biomarker for cancer diagnosis.

In a specific exemplary embodiment, the kit for diagnosing bile duct cancer may include all of the above-described 34 biomarkers as one set.

In still another exemplary embodiment, the present invention provides a kit for diagnosing bile duct cancer. The kit includes one or more biomarkers selected from the group consisting of miRNA hsa-miR-7107-5p, hsa-miR-4270, hsa-miR-1268a, hsa-miR-3162-3p, and hsa-miR-6729-5p, which have been discovered through the method for discovery of a miRNA biomarker for cancer diagnosis.

In a specific exemplary embodiment, the kit for diagnosing bile duct cancer may include all of the above-described 5 biomarkers as one set.

In a specific exemplary embodiment, the kit for diagnosing bile duct cancer may include all of the above-described 34 biomarkers and the above-described 5 biomarkers as one set.

In a specific exemplary embodiment, the kit for diagnosing bile duct cancer may utilize publicly-known constituent elements except for the biomarker portion. Further, a manual containing instructions (for example, a protocol) for performing the method described in the present invention may be included in the corresponding kit.

In still another exemplary embodiment, the present invention provides a kit for diagnosing pancreatic cancer. The kit includes one or more biomarkers selected from the group consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p, which have been discovered through the method for discovery of a miRNA biomarker for cancer diagnosis.

In a specific exemplary embodiment, the kit for diagnosing pancreatic cancer may include all of the above-described 23 biomarkers as one set.

In yet another exemplary embodiment, the present invention provides a kit for diagnosing pancreatic cancer. The kit includes one or more biomarkers selected from the group consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, which have been discovered through the method for discovery of a miRNA biomarker for cancer diagnosis.

In a specific exemplary embodiment, the kit for diagnosing pancreatic cancer may include all of the above-described 16 biomarkers as one set.

In a specific exemplary embodiment, the kit for diagnosing pancreatic cancer may include all of the above-described 23 biomarkers and the above-described 16 biomarkers as one set.

In a specific exemplary embodiment, the kit for diagnosing pancreatic cancer may utilize publicly-known constituent elements except for the biomarker portion. Further, a manual containing instructions (for example, a protocol) for performing the method described in the present invention may be included in the corresponding kit.

In a still yet exemplary embodiment, the present invention provides a computing device for diagnosing cancer. The computing device includes: a storing part for storing data; and a control part for calculation, in which the control part performs a process of diagnosing cancer when f(x)>0 as a result of a calculation by substitution of the expression level of a miRNA biomarker, which has been discovered through the method for discovery of a miRNA biomarker for cancer diagnosis, into the following SVM classifier function.

$$f(x) = \sum_{i=1}^{n} \alpha_i y_i \exp(-\gamma \|x_i - x\|^2) + b$$

(in the equation, $y_i$ means a y value of an i-th support vector, $x_i$ means an x value of the i-th support vector, $\alpha_i$ means a weight of the i-th support vector, N means the number of support vectors, $\gamma$ is a shape parameter of a radial basis function kernel, b is an intercept of a decision function, and x means a miRNA expression level vector of a patient to be diagnosed.)

In a specific exemplary embodiment, the control part may calculate an expression level of each miRNA biomarker in a peripheral blood sample by substitution of the expression level into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, and hsa-miR-888-3p, and a subject to be diagnosed may be bile duct cancer.

In a specific exemplary embodiment, the control part may calculate an expression level of each miRNA biomarker in a peripheral blood sample by substitution of the expression level into an SVM classifier function for a biomarker set consisting of miRNA hsa-miR-7107-5p, hsa-miR-4270, hsa-miR-1268a, hsa-miR-3162-3p, and hsa-miR-6729-5p, and a subject to be diagnosed may be bile duct cancer.

In a specific exemplary embodiment, the control part may calculate an expression level of each miRNA biomarker in a peripheral blood sample by substitution of the expression level into an SVM classifier function for a biomarker set consisting of miRNA hsa-miR-26b-5p, hsa-miR-214-5p, hsa-miR-191-3p, hsa-miR-127-5p, hsa-miR-128-2-5p, hsa-miR-580-5p, hsa-miR-593-5p, hsa-miR-653-3p, hsa-miR-1224-3p, hsa-miR-208b-5p, hsa-miR-1229-5p, hsa-miR-548g-3p, hsa-miR-513c-5p, hsa-miR-1825, hsa-miR-3126-5p, hsa-miR-3649, hsa-miR-3677-3p, hsa-miR-499b-5p, hsa-miR-4770, hsa-miR-4784, hsa-miR-5687, hsa-miR-5697, hsa-miR-6511a-3p, hsa-miR-6740-3p, hsa-miR-6773-5p, hsa-miR-6795-3p, hsa-miR-6814-3p, hsa-miR-6843-3p, hsa-miR-6884-3p, hsa-miR-6889-3p, hsa-miR-6892-5p, hsa-miR-7158-5p, hsa-miR-208a-3p, hsa-miR-888-3p, hsa-miR-7107-5p, hsa-miR-4270, hsa-miR-1268a, hsa-miR-3162-3p, and hsa-miR-6729-5p, and a subject to be diagnosed may be bile duct cancer.

In a specific exemplary embodiment, the control part may calculate an expression level of each miRNA biomarker in a peripheral blood sample by substitution of the expression level into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, and hsa-miR-425-3p, and a subject to be diagnosed may be pancreatic cancer.

In a specific exemplary embodiment, the control part may calculate an expression level of each miRNA biomarker in a peripheral blood sample by substitution of the expression level into an SVM classifier function for a biomarker set consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

In a specific exemplary embodiment, the control part may calculate an expression level of each miRNA biomarker in a peripheral blood sample by substitution of the expression level into an SVM classifier function for a biomarker set consisting of miRNA hsa-miR-378b, hsa-miR-27b-3p, hsa-miR-191-3p, hsa-miR-5583-5p, hsa-miR-3145-5p, hsa-miR-513a-5p, hsa-miR-877-5p, hsa-miR-2053, hsa-miR-3183, hsa-miR-490-5p, hsa-miR-4310, hsa-miR-642b-3p, hsa-miR-1269b, hsa-miR-5571-5p, hsa-miR-933, hsa-miR-5692a, hsa-miR-6069, hsa-miR-548ay-5p, hsa-miR-6763-5p, hsa-miR-6854-3p, hsa-miR-6854-5p, hsa-miR-7154-5p, hsa-miR-425-3p, hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed may be pancreatic cancer.

The present invention may provide a method for discovery of a novel biomarker for cancer diagnosis, particularly, a method for discovery of biomarker for diagnosis of bile duct cancer or pancreatic cancer.

The present invention may provide a method for discovery of a biomarker including high specificity and sensitivity by an inherent statistical approaching method, and may provide a method for diagnosing cancer, which significantly enhances the specificity and sensitivity of a diagnosis probability by developing a novel SVM classifier function capable of being associated with the discovered biomarker.

Further, when the discovered biomarker is utilized, a kit for diagnosing cancer and a computing device for diagnosing cancer, which includes these, may be implemented, and thus may make a diagnosis for bile duct cancer or pancreatic cancer early and precise by using a peripheral blood sample which is taken by particularly, a non-invasive method, and thus is friendly to the human body.

The technical problems which the present invention intends to solve are not limited to the technical effects which have been mentioned above, and still other technical effects which have not been mentioned will be apparently understood by a person of ordinary skill in the art to which the present invention pertains from the following description.

BRIEF DESCRIPTION OF THE DRAWINGS

FIG. 1 illustrates a method for discovery of a miRNA biomarker for cancer diagnosis according to an exemplary embodiment of the present invention, and a flowchart for the method for diagnosing cancer by using a novel SVM classifier function formula developed based on the method.

MODES FOR CARRYING OUT THE PREFERRED EMBODIMENTS

Reference will now be made in detail to the preferred embodiments of the present invention, examples of which are illustrated in the accompanying drawings. It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

Description will now be given in detail of a drain device and a refrigerator having the same according to an embodiment, with reference to the accompanying drawings.

Hereinafter, the present invention will be described in detail such that a person skilled in the art to which the present invention pertains can easily carry out the present invention. However, the present invention can be implemented in various different forms, and is not limited to the Examples described herein.

Performing Affymetrix miRNA Arrays:

1. Performance 1

After blood collected from a patient and a normal person was transferred to serum tubes and the tubes were sent to a laboratory while being contained in a cooling pack at 4° C., supernatant (serum) was separated by centrifuging the tubes at 3,000 rpm for 20 minutes. The total RNA in the serum was separated by using a serum miRNA purification kit manufactured by Genolution Inc. An OD 260/280 ratio was measured in order to check the purity of the extracted miRNA, and an electrophoresis of Agilent 2100 Bioanalyzer (Agilent Technologies, Palo Alto, USA) was performed by using Agilent RNA Nano 6000 LabChip Kit in order to confirm the state and concentration of the miRNA.

A microarray was performed on 241 RNA samples, and these samples were collected from 107 patients with bile duct cancer, 89 patients with pancreatic cancer, 11 patients with cholelithiasis, 5 patients with colon cancer, 7 patients with gastric cancer, 2 patients with gastrointestinal stromal tumor (GIST), and 20 normal persons. Bile duct cancer was diagnosed through ultrasonography, computed tomography (CT), magnetic resonance imaging (MRI), endoscopic retrograde cholangio-pancreatography (ERCP), percutaneous transhepatic cholangiography (PTC), endoscopic ultrasonography (EUS), proton emission tomography (PET), a serum tumor marker test, and a tissue test based on symptoms such as weight loss and fatigue, loss of appetite, nausea, vomiting, pain in the upper abdomen or solar plexus, and jaundice, and pancreatic cancer was diagnosed through ultrasonography, abdominal computed tomography (CT), magnetic resonance imaging (MRI), endoscopic retrograde cholangio-pancreatography (ERCP), endoscopic ultrasonography (EUS), proton emission tomography (PET), a serum tumor marker test, a laparoscopic test, and a tissue test based on symptoms such as abdominal pain and weight loss, jaundice, maldigestion, and the occurrence or aggravation of diabetes. Among the other diseases, cholelithiasis was diagnosed by using a blood test, an endoscopic test, and a radiological examination, and the radiological examination was performed when a gallstone was shown primarily on ultrasonography, or a gallstone was shown on computed tomography (CT). Colon cancer was definitively diagnosed after cancer cells were found through a tissue test via colonoscopy based on change in bowel habits, diarrhea, constipation, bloody stools or sticky mucus stools, abdominal pain, abdominal distension, fatigue, loss of appetite, indigestion, abdominal mass (a lump is felt in the stomach), and the like, which are main symptoms. For the diagnosis of colon cancer, a digital rectal examination, a stool examination, colonography, computed tomography (CT), magnetic resonance imaging (MRI), a blood test, and the like were additionally used. Gastric cancer was diagnosed by gastroscopy, a gastrointestinal contrast examination, and computed tomography (CT) based on symptoms such as heartburn, nausea, vomiting, abdominal pain, dizziness, difficulty in swallowing food (dysphagia), weight loss, fatigue, and melaena, and the case where cancer cells were found by a tissue test through gastroscopy was definitively diagnosed with gastric cancer. After gastrointestinal stromal tumor (GIST) was diagnosed through gastroscopy, endoscopic ultrasonography, computed tomography (CT), and the like, GIST was definitively diagnosed after being confirmed through immunostaining of proteins, which is called as a "kit (which examines genetic mutations)" that gastrointestinal stromal tumor inherently has along with a tissue test for the exact diagnosis. The normal person does not have other cancer diagnosis records including the bile duct cancer, pancreatic cancer, cholelithiasis, colon cancer, gastric cancer, and gastrointestinal stromal tumor (GIST), and a patient who did not currently have any specific disease was decided to be normal.

The Affymetrix Genechip miRNA 4.0 array experiment followed the manufacturer's protocol.

241 RNA samples each having 130 ng were labeled by using FlashTag™ Biotin RNA Labeling Kit (Genisphere, Hatfield, Pa., USA), and then were left to stand at 99° C. for 5 minutes and at 45° C. for 5 minutes. RNA-array hybridization was performed in an Affymetrix® 450 Fluidics Station instrument for 16 hours. The completely hybridized chip was washed with water in a Genechip Fluidics Station 450 (Affymetrix, Santa Clara, Calif., United States), and then was scanned by using an Affymetrix GCS 3000 canner (Affymetrix, Santa Clara, Calif., United States). After the scanning was completed, chip QC and RNA normalization were performed by using an Affymetrix® GeneChip™ Expression Console software.

After rescreening of a secondary candidate to which a primary candidate screening and an SCAD penalty function were applied through the microarray analysis through a 10-fold cross validation 100 times, 34 final miRNA biomarkers for bile duct cancer were selected based on the calculation of specific sensitivity and specificity for bile duct cancer with respect to each of the rescreened candidates (Table 1), and 23 final miRNA biomarkers for pancreatic cancer were selected by the same method (Table 3).

Information on the patients is shown in the following Tables 5 to 9.

TABLE 5

| Sample | | Persons |
| --- | --- | --- |
| Bile duct cancer | | 107 |
| Pancreatic cancer | | 89 |
| Other diseases | Cholelithiasis | 11 |
| | Colon cancer | 5 |
| | Gastric cancer | 7 |
| | GIST | 2 |
| Normal | | 20 |
| total | | 241 |

TABLE 6

| Ages | Gender | |
| --- | --- | --- |
| | Male | Female |
| 30~49 | 7 | 1 |
| 50~69 | 42 | 26 |
| 70~89 | 21 | 10 |
| Total | 70 | 37 |

Information on the ages and gender of patients with bile duct cancer (107 persons)

TABLE 7

| Ages | Gender | |
| --- | --- | --- |
| | Male | Female |
| 30~49 | 7 | 2 |
| 50~69 | 38 | 18 |
| 70~89 | 18 | 6 |
| Total | 63 | 26 |

Information on the ages and gender of patients with pancreatic cancer (89 persons)

TABLE 8

| Ages | Gender | |
| --- | --- | --- |
| | Male | Female |
| 30~49 | 5 | 0 |
| 50~69 | 7 | 8 |
| 70~89 | 3 | 2 |
| Total | 15 | 10 |

Information on the ages and gender of patients with other diseases (25 persons)

TABLE 9

| Ages | Gender | |
| --- | --- | --- |
| | Male | Female |
| 20~29 | 10 | 2 |
| 30~49 | 4 | 3 |
| 50~69 | 0 | 1 |
| Total | 14 | 6 |

Information on the ages and gender of normal persons (20 persons)

2. Performance 2

After blood collected from a patient and a normal person was transferred to serum tubes and the tubes were sent to a laboratory while being contained in a cooling pack at 4° C., supernatant (serum) was separated by centrifuging the tubes at 3,000 rpm for 20 minutes. The total RNA in the serum was separated by using a serum miRNA purification kit manufactured by Genolution Inc. An OD 260/280 ratio was measured in order to check the purity of the extracted miRNA, and an electrophoresis of Agilent 2100 Bioanalyzer (Agilent Technologies, Palo Alto, USA) was performed by using Agilent RNA Nano 6000 LabChip Kit in order to confirm the state and concentration of the miRNA.

A microarray was performed on 232 RNA samples, and these samples were collected from 101 patients with bile duct cancer, 88 patients with pancreatic cancer, 10 patients with cholelithiasis, 5 patients with colon cancer, 7 patients with gastric cancer, 2 patients with gastrointestinal stromal tumor (GIST), and 19 normal persons. Bile duct cancer was diagnosed through ultrasonography, computed tomography (CT), magnetic resonance imaging (MRI), endoscopic retrograde cholangio-pancreatography (ERCP), percutaneous transhepatic cholangiography (PTC), endoscopic ultrasonography (EUS), proton emission tomography (PET), a serum tumor marker test, and a tissue test based on symptoms such as weight loss and fatigue, loss of appetite, nausea, vomiting, pain in the upper abdomen or solar plexus, and jaundice, and pancreatic cancer was diagnosed through ultrasonography, abdominal computed tomography (CT), magnetic resonance imaging (MRI), endoscopic retrograde cholangio-pancreatography (ERCP), endoscopic ultrasonography (EUS), proton emission tomography (PET), a serum tumor marker test, a laparoscopic test, and a tissue test based on symptoms such as abdominal pain and weight loss, jaundice, maldigestion, and the occurrence or aggravation of diabetes. Among the other diseases, cholelithiasis was diagnosed by using a blood test, an endoscopic test, and a radiological examination, and the radiological examination was performed when a gallstone was shown primarily on ultrasonography, or a gallstone was shown on computed tomography (CT). Colon cancer was definitively diagnosed after cancer cells were found through a tissue test via colonoscopy based on change in bowel habits, diarrhea, constipation, bloody stools or sticky mucus stools, abdominal pain, abdominal distension, fatigue, loss of appetite, indigestion, abdominal mass (a lump is felt in the stomach), and the like, which are main symptoms. For the diagnosis of colon cancer, a digital rectal examination, a stool examination, colonography, computed tomography (CT), magnetic resonance imaging (MRI), a blood test, and the like were additionally used. Gastric cancer was diagnosed by gastroscopy, a gastrointestinal contrast examination, and computed tomography (CT) based on symptoms such as heartburn, nausea, vomiting, abdominal pain, dizziness, difficulty in swallowing food (dysphagia), weight loss, fatigue, and melaena, and the case where cancer cells were found by a tissue test through gastroscopy was definitively diagnosed with gastric cancer. After gastrointestinal stromal tumor (GIST) was diagnosed through gastroscopy, endoscopic ultrasonography, computed tomography (CT), and the like, GIST was definitively diagnosed after being confirmed through immunostaining of proteins, which is called as a "kit (which examines genetic mutations)" that gastrointestinal stromal tumor inherently has along with a tissue test for the exact diagnosis. The normal person does not have other cancer diagnosis records including the bile duct cancer, pancreatic cancer, cholelithiasis, colon cancer, gastric cancer, and gastrointestinal stromal tumor (GIST), and a patient who did not currently have any specific disease was decided to be normal.

The Affymetrix Genechip miRNA 4.0 array experiment followed the manufacturer's protocol.

241 RNA samples each having 130 ng were labeled by using FlashTag™ Biotin RNA Labeling Kit (Genisphere, Hatfield, Pa., USA), and then were left to stand at 99° C. for 5 minutes and at 45° C. for 5 minutes. RNA-array hybridization was performed in an Affymetrix® 450 Fluidics Station instrument for 16 hours. The completely hybridized chip was washed with water in a Genechip Fluidics Station 450 (Affymetrix, Santa Clara, Calif., United States), and then was scanned by using an Affymetrix GCS 3000 canner (Affymetrix, Santa Clara, Calif., United States). After the scanning was completed, chip QC and RNA normalization were performed by using an Affymetrix® GeneChip™ Expression Console software.

After rescreening of a secondary candidate to which a primary candidate screening and an SCAD penalty function were applied through the microarray analysis through a 10-fold cross validation 100 times, 5 final miRNA biomarkers for bile duct cancer were selected based on the calculation of specific sensitivity and specificity for bile duct cancer with respect to each of the rescreened candidates (Table 2), and 16 final miRNA biomarkers for pancreatic cancer were selected by the same method (Table 4).

Information on the patients is shown in the following Tables 10 to 14.

TABLE 10

| Sample | | Persons |
|---|---|---|
| Bile duct cancer | | 101 |
| Pancreatic cancer | | 88 |
| Other diseases | Cholelithiasis | 10 |
| | Colon cancer | 5 |
| | Gastric cancer | 7 |
| | GIST | 2 |
| Normal | | 19 |
| total | | 232 |

TABLE 11

| | Gender | |
|---|---|---|
| Ages | Male | Female |
| 30~49 | 7 | 1 |
| 50~69 | 39 | 25 |
| 70~89 | 19 | 10 |
| Total | 62 | 36 |

Information on the ages and gender of patients with bile duct cancer (101 persons)

TABLE 12

| | Gender | |
|---|---|---|
| Ages | Male | Female |
| 30~49 | 7 | 2 |
| 50~69 | 37 | 18 |
| 70~89 | 18 | 6 |
| Total | 62 | 26 |

Information on the ages and gender of patients with pancreatic cancer (88 persons)

TABLE 13

| | Gender | |
|---|---|---|
| Ages | Male | Female |
| 30~49 | 4 | 0 |
| 50~69 | 7 | 8 |
| 70~89 | 3 | 2 |
| Total | 14 | 10 |

Information on the ages and gender of patients with other diseases (24 persons)

TABLE 14

| | Gender | |
|---|---|---|
| Ages | Male | Female |
| 20~29 | 9 | 2 |
| 30~49 | 4 | 3 |
| 50~69 | 0 | 1 |
| Total | 13 | 6 |

Information on the ages and gender of normal persons (19 persons)

Verification of Cancer Diagnosis Performance of miRNA Biomarker

1. Verification of Diagnosis Algorithm Performance Using Bile Duct Cancer Marker (1) The following function $$f(x) = \sum_{i=1}^{n} \alpha_i y_i \exp(-\gamma \|x_i - x\|^2) + b$$

was completed by using each expression level x1, x2, . . . , x34 of 34 miRNA biomarkers for the selected bile duct cancer with respect to patients with bile duct cancer (101 persons) and patients with non-bile duct cancer (65 persons), and a diagnostic formula which predicts that by substitution of 34 miRNA data x of new patients into the function, the case where f(x)>0 is diagnosed with bile duct cancer (Y=1) and the case where f(x) is not >0 is diagnosed with normal (Y=0) was developed.

In order to verify the performance of the early diagnostic formula for bile duct cancer, the process of discovering the biomarker previously described was repeated with respect to each training data through a 10-fold cross validation 100 times, and the averages of sensitivity and specificity, in which the process was applied to the test data, were calculated, and as a result, a result with a sensitivity of 0.85 and a specificity of 0.72 was obtained. Through the result, it was proven that the diagnosis algorithm using the 34 discovered miRNA biomarkers had excellent bile duct cancer diagnosis ability.

(2) The following function $$f(x) = \sum_{i=1}^{n} \alpha_i y_i \exp(-\gamma \|x_i - x\|^2) + b$$

was completed by using each expression level x1, x2, ..., x5 of 5 miRNA biomarkers for the selected bile duct cancer with respect to patients with bile duct cancer (101 persons) and patients with non-bile duct cancer (63 persons), and a diagnostic formula which predicts that by substitution of 5 miRNA data x of new patients into the function, the case where f(x)>0 is diagnosed with bile duct cancer (Y=1) and the case where f(x) is not >0 is diagnosed with normal (Y=0) was developed.

In order to verify the performance of the bile duct cancer early diagnostic formula, the process of discovering the biomarker previously described was repeated with respect to each training data through a 10-fold cross validation 100 times, and the averages of sensitivity and specificity, in which the process was applied to the test data, were calculated, and as a result, a result with a sensitivity of 0.77 and a specificity of 0.69 was obtained. Through the result, it was proven that the diagnosis algorithm using the 5 discovered miRNA biomarkers had excellent bile duct cancer diagnosis ability.

2. Verification of Diagnosis Algorithm Performance Using Pancreatic Cancer Marker (1) The following function $$f(x) = \sum_{i=1}^{n} \alpha_i y_i \exp(-\gamma \|x_i - x\|^2) + b$$

was completed by using each expression level x1, x2, ..., x23 of 23 miRNA biomarkers for the selected bile duct cancer with respect to patients with pancreatic cancer (89 persons) and patients with non-bile duct cancer (65 persons), and a diagnostic formula which predicts that by substitution of 23 miRNA data x of new patients into the function, the case where f(x)>0 is diagnosed with pancreatic cancer (Y=1) and the case where f(x) is not >0 is diagnosed with normal (Y=0) was developed.

In order to verify the performance of the pancreatic cancer early diagnostic formula, the process of discovering the biomarker previously described was repeated with respect to each training data through a 10-fold cross validation 100 times, and the averages of sensitivity and specificity, in which the process was applied to the test data, were calculated, and as a result, a result with a sensitivity of 0.96 and a specificity of 0.92 was obtained. Through the result, it was proven that the diagnosis algorithm using the 23 discovered miRNA biomarkers had excellent pancreatic cancer diagnosis ability.

(2) The following function $$f(x) = \sum_{i=1}^{n} \alpha_i y_i \exp(-\gamma \|x_i - x\|^2) + b$$

was completed by using each expression level x1, x2, ..., x16 of 16 miRNA biomarkers for the selected pancreatic cancer with respect to patients with pancreatic cancer (88 persons) and patients with non-pancreatic cancer (63 persons), and a diagnostic formula which predicts that by substitution of 16 miRNA data x of new patients into the function, the case where f(x)>0 is diagnosed with pancreatic cancer (Y=1) and the case where f(x) is not >0 is diagnosed with normal (Y=0) was developed.

In order to verify the performance of the pancreatic cancer early diagnostic formula, the process of discovering the biomarker previously described was repeated with respect to each training data through a 10-fold cross validation 100 times, and the averages of sensitivity and specificity, in which the process was applied to the test data, were calculated, and as a result, a result with a sensitivity of 0.92 and a specificity of 0.90 was obtained. Through the result, it was proven that the diagnosis algorithm using the 16 discovered miRNA biomarkers had excellent pancreatic cancer diagnosis ability.

Although preferred Examples of the present invention have been described in detail hereinabove, the right scope of the present invention is not limited thereto, and it should be clearly understood that many variations and modifications of those skilled in the art using the basic concept of the present invention, which is defined in the following claims, will also fall within the right scope of the present invention.

The invention claimed is:

1. A method for diagnosing cancer, the method comprising:
    obtaining a peripheral blood sample from a patient;
    centrifuging the peripheral blood sample to obtain a serum;
    separating RNA in the serum;
    purifying the RNA to obtain a purified RNA sample;
    measuring the purified RNA sample for an expression level of at least one miRNA biomarker; and
    assigning a disease condition of cancer based on determining
    when f(x)>0 by substitution of the expression level of the miRNA biomarker, from the purified RNA sample into the following SVM classifier function:

$$f(x) = \sum_{i=1}^{n} \alpha_i y_i \exp(-\gamma \|x_i - x\|^2) + b$$

in the equation, $y_i$ means a y value of an i-th support vector, $x_i$ means an x value of the i-th support vector, $\alpha_i$ means a weight of the i-th support vector, N means the number of support vectors, $\gamma$ is a shape parameter of a radial basis function kernel, b is an intercept of a decision function, and x means a miRNA expression level vector of a patient to be diagnosed,
    wherein the SVM classifier function is performed by a computing device,
    wherein the computing device comprises a storing part for storing data and a control part for calculating the SVM classifier function,
    wherein the at least one miRNA biomarkers are determined in a method comprising:
        (i) screening differential expression miRNAs in a sample by using a microarray analysis;
        (ii) rescreening the screened differential expression miRNAs by applying an SCAD penalty function; and
        (iii) selecting one or more of the rescreened differential expression miRNAs as a biomarker based on a sensitivity and specificity calculation result of a cancer prediction model, and
    wherein the at least one miRNA biomarkers are used for the purpose of diagnosis and treatment of bile duct cancer or pancreatic cancer.

2. The method of claim 1, wherein the diagnosis method is performed by substitution of an expression level of each miRNA biomarker in a peripheral blood sample into an SVM classifier function for a biomarker set consisting of miRNA hsa-miR-7107-5p, hsa-miR-4270, hsa-miR-1268a, hsa-miR-3162-3p, and hsa-miR-6729-5p, and a subject to be diagnosed is bile duct cancer.

3. The method of claim 1, wherein the diagnosis method is performed by substitution of the expression level of each miRNA biomarker in a peripheral blood sample into an SVM classifier function for a biomarker set consisting of miRNA hsa-miR-1228-3p, hsa-miR-1469, hsa-miR-4530, hsa-miR-4532, hsa-miR-4721, hsa-miR-4741, hsa-miR-486-5p, hsa-miR-5100, hsa-miR-5787, hsa-miR-6087, hsa-miR-642a-3p, hsa-miR-642b-3p, hsa-miR-6800-5p, hsa-miR-6803-5p, hsa-miR-7704, and hsa-miR-6808-5p, and a subject to be diagnosed is pancreatic cancer.

* * * * *